United States Patent
Han et al.

(10) Patent No.: US 10,573,825 B2
(45) Date of Patent: Feb. 25, 2020

(54) COMPOUND AND ORGANIC LIGHT-EMITTING DEVICE INCLUDING THE SAME

(71) Applicant: Samsung Display Co., Ltd., Yongin-si, Gyeonggi-do (KR)

(72) Inventors: Sanghyun Han, Yongin-si (KR); Sooyon Kim, Yongin-si (KR); Hyejin Jung, Yongin-si (KR); Youngkook Kim, Yongin-si (KR); Seokhwan Hwang, Yongin-si (KR)

(73) Assignee: Samsung Display Co., Ltd. (KR)

( * ) Notice: Subject to any disclaimer, the term of this patent is extended or adjusted under 35 U.S.C. 154(b) by 71 days.

(21) Appl. No.: 15/594,272

(22) Filed: May 12, 2017

(65) Prior Publication Data

US 2017/0331051 A1    Nov. 16, 2017

(30) Foreign Application Priority Data

May 13, 2016   (KR) .................. 10-2016-0058766

(51) Int. Cl.
| | | |
|---|---|---|
| H01L 29/08 | (2006.01) |
| H01L 51/00 | (2006.01) |
| C07D 311/78 | (2006.01) |
| C07D 407/04 | (2006.01) |
| C09K 11/02 | (2006.01) |

(Continued)

(52) U.S. Cl.
CPC ........ *H01L 51/0073* (2013.01); *C07D 311/78* (2013.01); *C07D 407/04* (2013.01); *C09K 11/02* (2013.01); *C09K 11/06* (2013.01); *H01L 51/0052* (2013.01); *H01L 51/0058* (2013.01); *H01L 51/0077* (2013.01); *C09K 2211/1007* (2013.01); *C09K 2211/1011* (2013.01); *C09K 2211/1018* (2013.01); *H01L 27/3244* (2013.01); *H01L 51/506* (2013.01);

(Continued)

(58) Field of Classification Search
USPC .......................................................... 257/40
See application file for complete search history.

(56) References Cited

U.S. PATENT DOCUMENTS

| 5,972,247 A | 10/1999 | Shi et al. |
| 6,465,115 B2 | 10/2002 | Shi et al. |

(Continued)

FOREIGN PATENT DOCUMENTS

| CN | 10-2925139 A | 2/2013 |
| JP | 08-012600 A | 1/1996 |

(Continued)

*Primary Examiner* — Caleb E Henry
(74) *Attorney, Agent, or Firm* — Innovation Counsel LLP

(57) ABSTRACT

Provided are a compound represented by Formula 1 and an organic light-emitting device including the same:

<Formula 1>

$Ar_1$, $Ar_2$ wherein descriptions of Formula 1 are provided in the detailed description of the present specification.

18 Claims, 1 Drawing Sheet

(51) Int. Cl.
*C09K 11/06* (2006.01)
*H01L 27/32* (2006.01)
*H01L 51/50* (2006.01)

(52) U.S. Cl.
CPC ...... *H01L 51/5012* (2013.01); *H01L 51/5072* (2013.01); *H01L 51/5092* (2013.01); *H01L 51/5096* (2013.01)

(56) References Cited

U.S. PATENT DOCUMENTS

| | | | |
|---|---|---|---|
| 6,596,415 | B2 | 7/2003 | Shi et al. |
| 7,053,255 | B2 | 5/2006 | Ikeda et al. |
| 7,233,019 | B2 | 6/2007 | Ionkin et al. |
| 9,249,301 | B2 | 2/2016 | Schoeley et al. |
| 10,256,416 | B2 * | 4/2019 | Lee .................. H01L 51/0073 |
| 2004/0214035 | A1 | 10/2004 | Ikeda et al. |
| 2005/0238910 | A1 | 10/2005 | Ionkin et al. |
| 2009/0004485 | A1 * | 1/2009 | Zheng .................. C07C 255/09 428/446 |
| 2010/0032658 | A1 | 2/2010 | Lee et al. |
| 2013/0306958 | A1 * | 11/2013 | Ito ........................ C07D 405/10 257/40 |
| 2016/0118593 | A1 | 4/2016 | Kim et al. |
| 2016/0190481 | A1 | 6/2016 | Han et al. |
| 2016/0233439 | A1 * | 8/2016 | Burschka ............ H01L 51/0083 |

FOREIGN PATENT DOCUMENTS

| | | |
|---|---|---|
| JP | 2000-003782 A | 1/2000 |
| KR | 10-2006-0006760 A | 1/2006 |
| KR | 10-2010-0007780 A | 1/2010 |
| KR | 10-2014-0144276 A | 12/2014 |
| KR | 10-2016-0048282 A | 5/2016 |
| KR | 10-2016-0081685 A | 7/2016 |

\* cited by examiner

10

| 190 |
|-----|
| 150 |
| 110 |

COMPOUND AND ORGANIC LIGHT-EMITTING DEVICE INCLUDING THE SAME

CROSS-REFERENCE TO RELATED APPLICATION

This application claims the benefit of Korean Patent Application No. 10-2016-0058766 filed on May 13, 2016 in the Korean Intellectual Property Office, the disclosure of which is incorporated herein in its entirety by reference.

BACKGROUND

1. Field

One or more embodiments related to a compound and an organic light-emitting device including the same.

2. Description of the Related Art

Organic light-emitting devices are self-emission devices that produce full-color images, and also have wide viewing angles, high contrast ratios, short response times, as well as excellent characteristics in terms of brightness, driving voltage, and response speed.

An example of such organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state, thereby generating light.

SUMMARY

One or more embodiments include a material having an excellent electron transport capability or a light-emitting material and an organic light-emitting device using the same.

Additional aspects will be set forth in part in the description which follows and, in part, will be apparent from the description, or may be learned by practice of the presented embodiments.

According to one or more embodiments, a compound is represented by Formula 1:

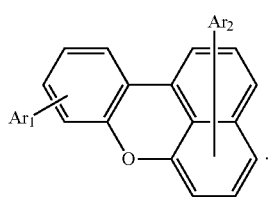

<Formula 1>

In Formula 1,

Each of $Ar_1$ and $Ar_2$ is independently selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $c_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$) heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $Si(Q_1)(Q_2)(Q_3)$, $P(=O)(Q_4)(Q_5)$, $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group(aryloxy), $C_6$-$C_{60}$ arylthio group(arylthio), $C_2$-$C_{60}$ heteroaryl group, a monovalent non-aromatic condensed polycyclic group, a monovalent non-aromatic condensed heteropolycyclic group, $-N(Q_{11})(Q_{12})$, $-Si(Q_{13})(Q_{14})(Q_{15})$, and $-B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and Each of $Q_1$ to $Q_5$, $Q_{11}$ to $Q_{17}$, and $Q_{21}$ to $Q_{27}$ is independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more embodiments, an organic light-emitting device includes: a first electrode; a second electrode facing the first electrode; and an organic layer that is disposed between the first electrode and the second electrode and includes an emission layer, wherein the organic layer includes the compound of Formula 1.

According to one or more embodiments, a flat panel display apparatus includes the organic light-emitting device, wherein a first electrode of the organic light-emitting device is electrically connected to a source electrode or a drain electrode of a thin film transistor.

BRIEF DESCRIPTION OF THE DRAWING

These and/or other aspects will become apparent and more readily appreciated from the following description of the embodiments, taken in conjunction with FIG. 1, which is a schematic diagram of a structure of an organic light-emitting device according to an embodiment of the present disclosure.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list. A compound according to an embodiment of the present disclosure is represented by Formula 1:

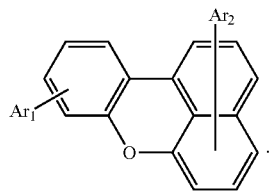

<Formula 1>

In Formula 1,

Each of $Ar_1$ and $Ar_2$ is independently be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, Si($Q_1$)($Q_2$)($Q_3$), P(=O)($Q_4$)($Q_5$), $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group(aryloxy), $C_6$-$C_{60}$ arylthio group(arylthio), $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and $Q_1$ to $Q_5$, $Q_{11}$ to $Q_{17}$, and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

A blue emission compound having a diphenylanthracene structure in its center and an aryl group substituted at its end, which is a blue emission material, and an organic light-emitting device using the blue emission compound are disclosed. However, light-emission efficiency and brightness of the organic light-emitting device are not sufficient.

Also, although an organic light-emitting device using a substituted pyrene-based compound is disclosed, blue color purity is low, and thus, it is difficult to embody deep blue and a full-color display.

Accordingly, aspects of embodiments provide a compound represented by Formula 1 and an organic light-emitting device including the compound. The compound of Formula 1 according to an embodiment has excellent electric characteristics, high charge transport capability, and high emission capability. In addition, since the compound of Formula 1 according to an embodiment has a high glass transition temperature and is able to prevent crystallization, the organic light-emitting device including the compound of Formula 1 may have high efficiency, low voltage, high brightness, and long lifespan.

Substituents of Formula 1 will now be described in detail.

In an embodiment, in Formula 1, $Ar_1$ and $Ar_2$ may each independently be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In an embodiment, in Formula 1, $Ar_1$ and $Ar_2$ may each independently be represented by one of Formulae 2a to 2m:

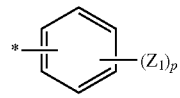

2a

-continued

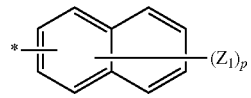

2b

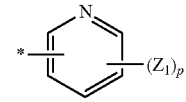

2c

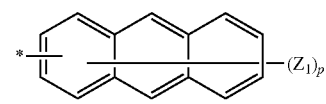

2d

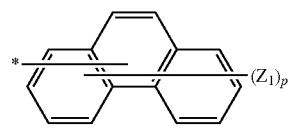

2e

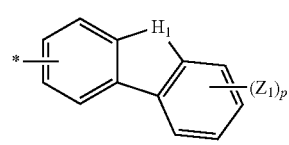

2f

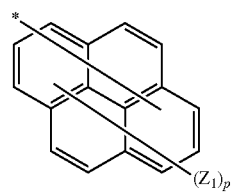

2g

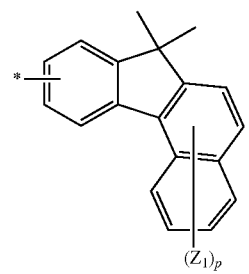

2h

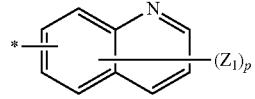

2i

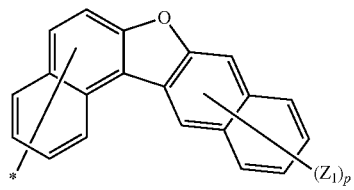

2j

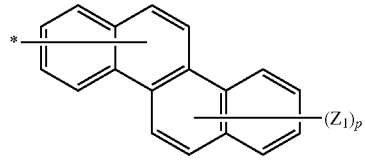

2k

-continued

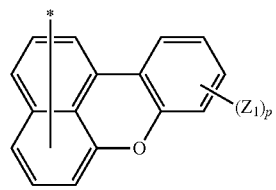

21

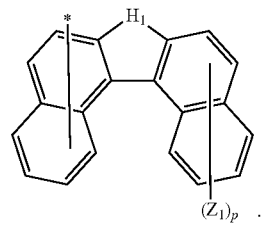

2m

In Formulae 2a to 2m, $H_1$ may be $SiR_{21} R_{22}$, $CR_{23}R_{24}$, O, or S, Zi may be selected from hydrogen, deuterium, a cyano group, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, $SiR_{31}R_{32}R_{33}$, P(=O) $R_{34}R_{35}$, $R_{21}$ to $R_{24}$ and $R_{31}$ to $R_{35}$ may each independently be selected from hydrogen, deuterium, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, p may be an integer of 1 to 9, and \* indicates a binding site.

In an embodiment, Formula 1 may be Formula 2:

<Formula 2>

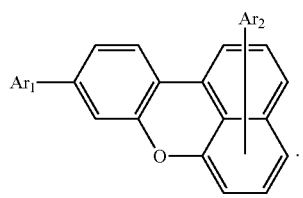

In an embodiment, Formula 1 may be Formula 3:

<Formula 3>

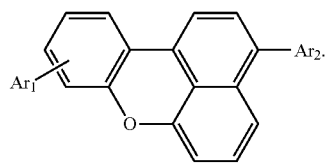

In an embodiment, Formula 1 may be Formula 4:

<Formula 4>

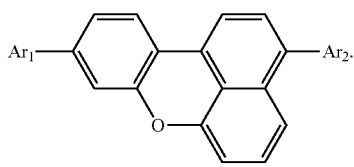

Regarding Formulae 2 to 4, definitions of substituents are the same as provided above.

In an embodiment, the compound of Formula 1 may be one of compounds illustrated below:

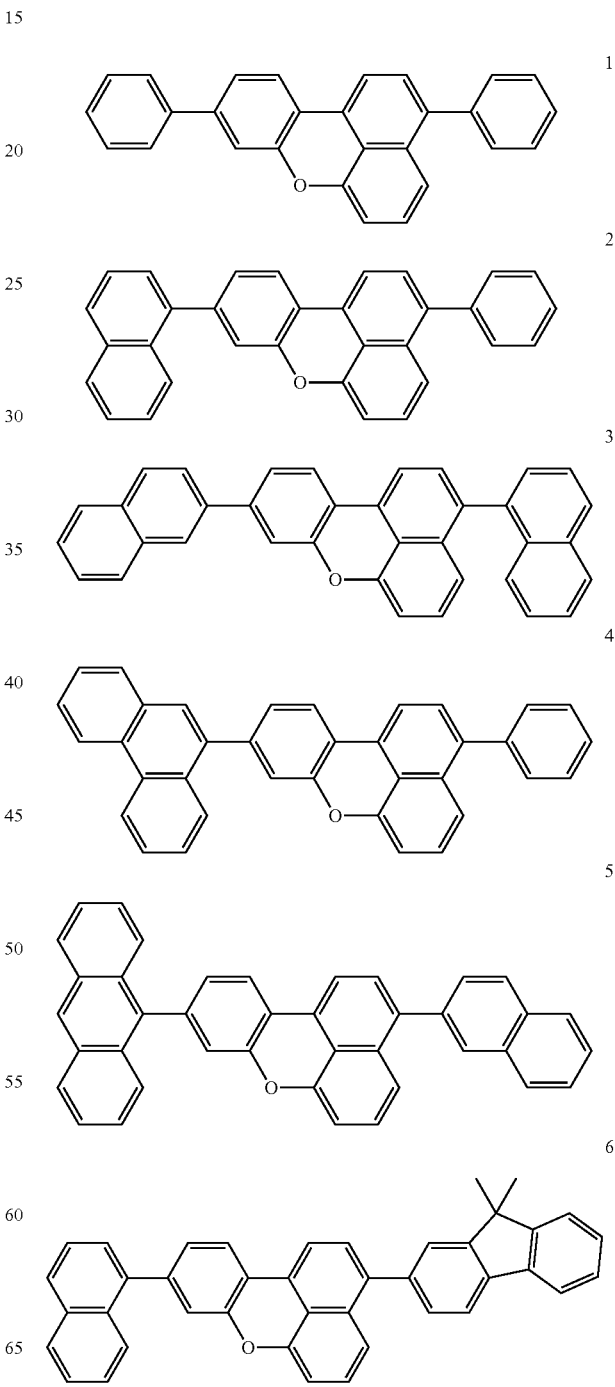

7
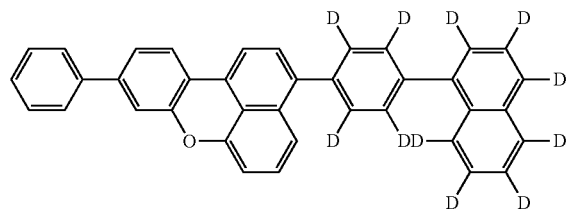
8
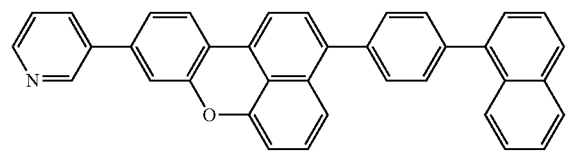
9
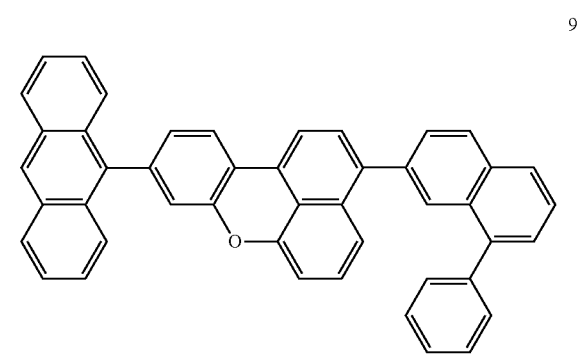
10
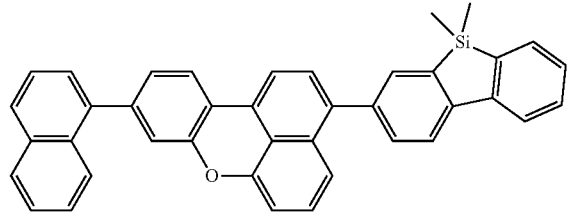
11
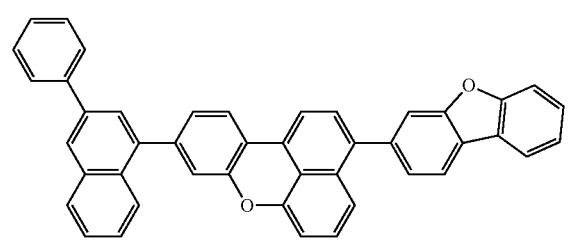
12
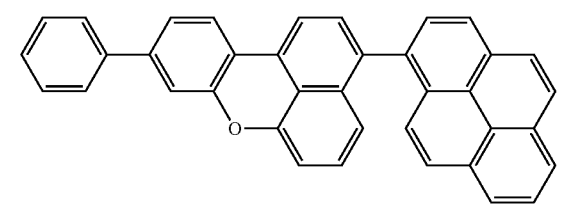
13
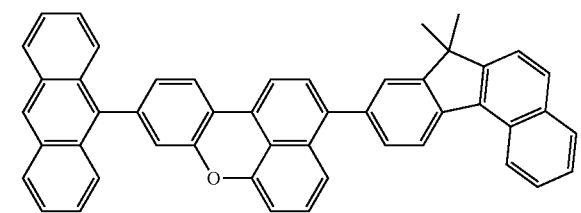
14
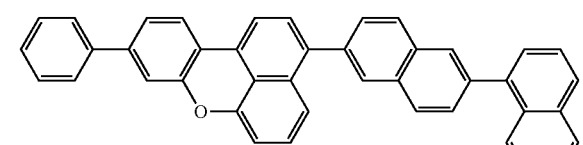
15
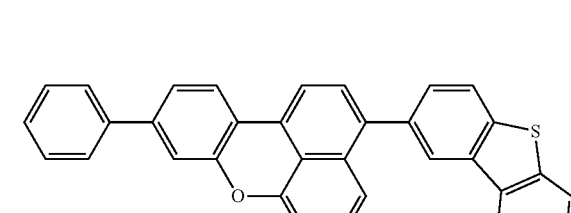
16
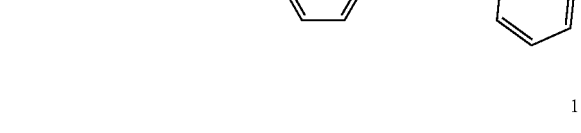
17
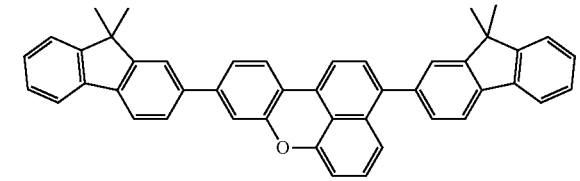
18
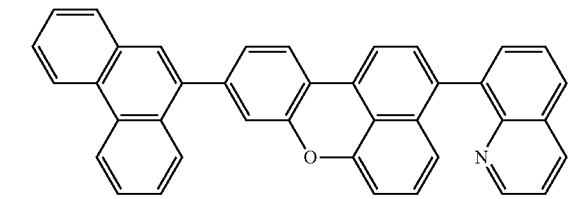
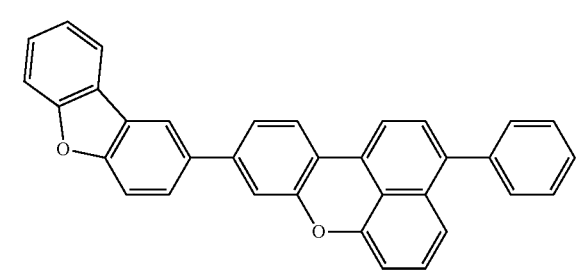

19
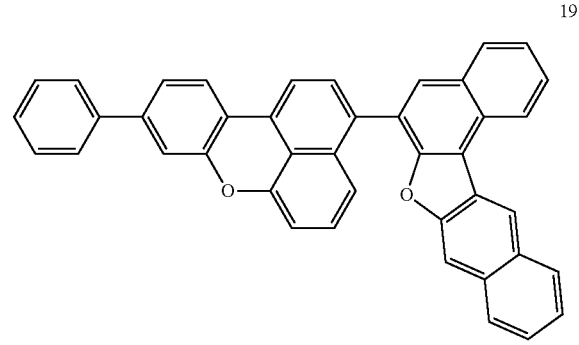
20
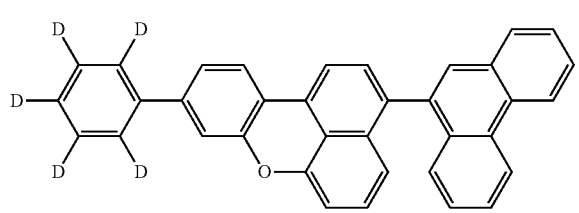
21
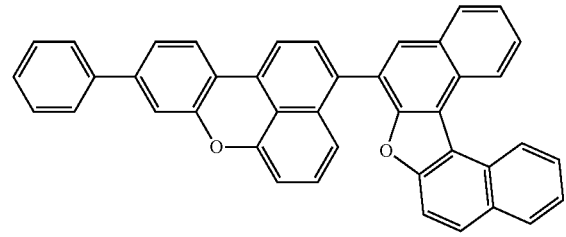
22
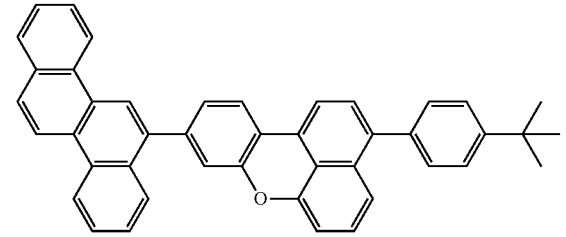
23
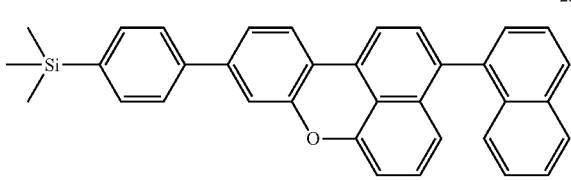
24
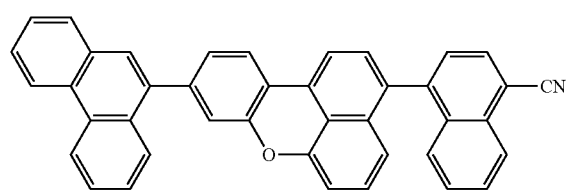
25
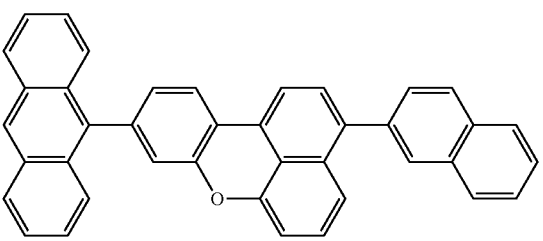
26
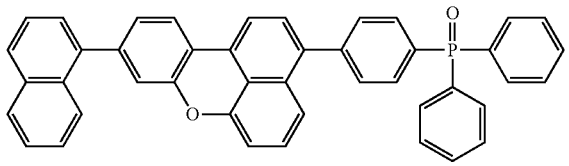
27
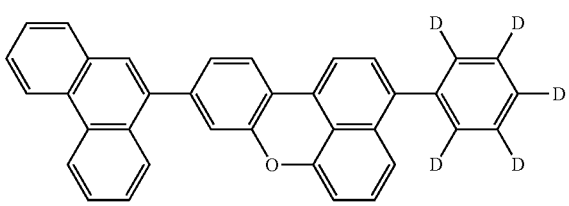
28
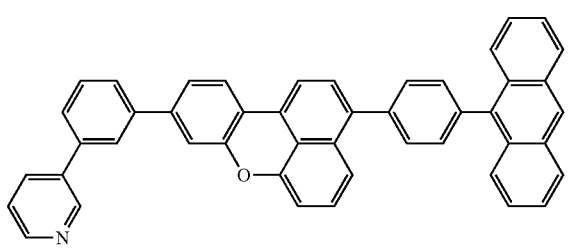
29
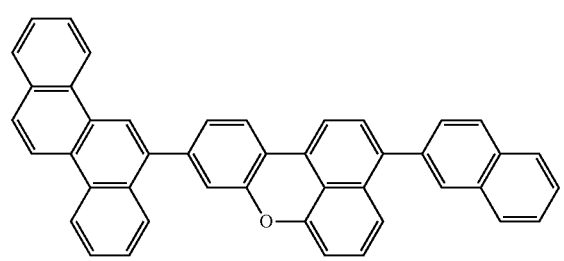
30
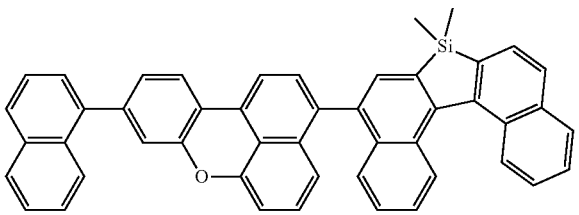

-continued

31
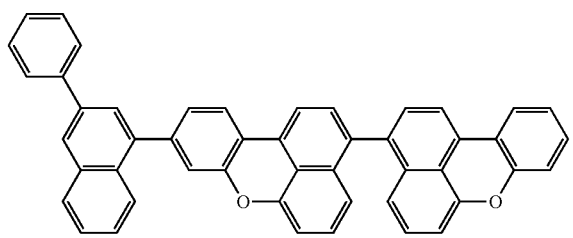

32
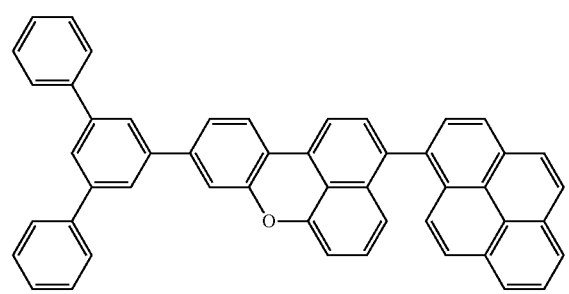

33
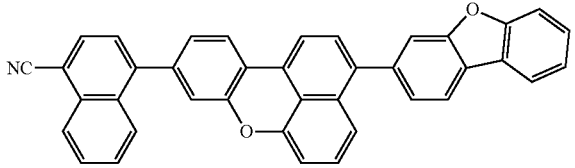

34
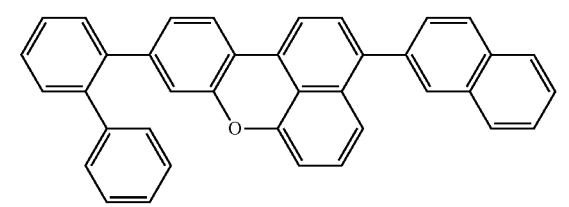

35
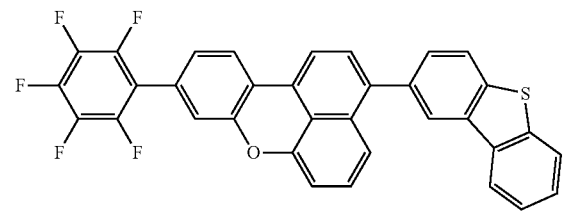

36
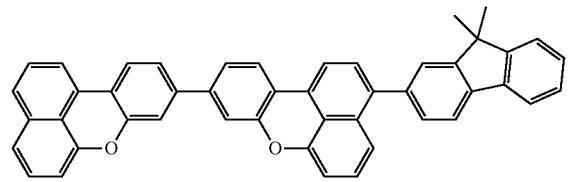

-continued

37
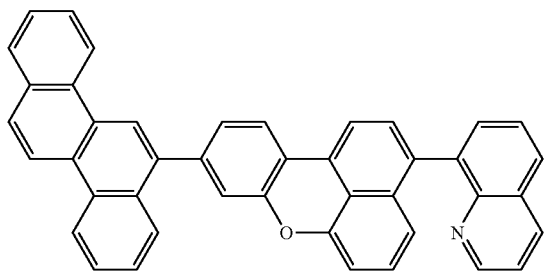

38
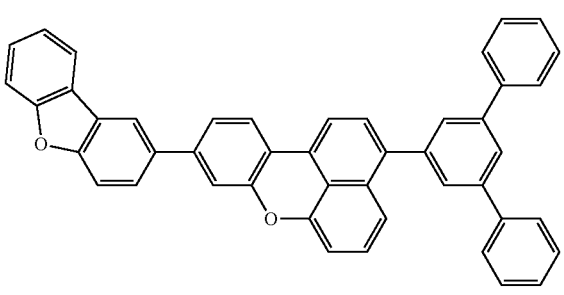

39
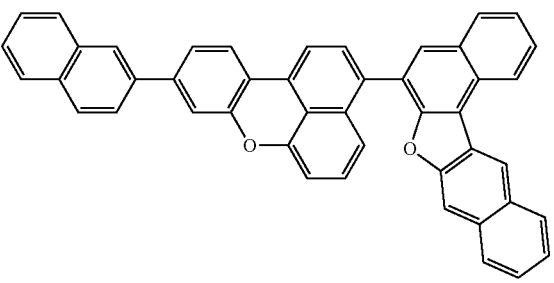

40
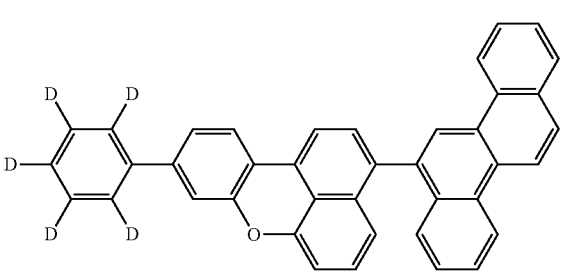

The term "organic layer" used herein refers to a single layer and/or a plurality of layers disposed between the first electrode and the second electrode of an organic light-emitting device. A material included in the "organic layer" is not limited to an organic material.

FIG. 1 is a schematic view of an organic light-emitting device 10 according to an embodiment. The organic light-emitting device 10 includes a first electrode 110, an organic layer 150, and a second electrode 190.

Hereinafter, the structure of an organic light-emitting device according to an embodiment and a method of manufacturing an organic light-emitting device according to an embodiment will be described in connection with FIG. 1.

In FIG. 1, a substrate may be additionally disposed under the first electrode 110 or above the second electrode 190. The substrate may be a glass substrate or a transparent plastic substrate, each having excellent mechanical strength, thermal stability, transparency, surface smoothness, ease of handling, and water resistance.

The first electrode 110 may be formed by, for example, depositing or sputtering a material for forming the first electrode 110 on the substrate. When the first electrode 110 is an anode, the material for forming the first electrode 110 may be selected from materials with a high work function to facilitate hole injection. The first electrode 110 may be a reflective electrode, a semi-transmissive electrode, or a transmissive electrode. The material for forming the first electrode 110 may be a transparent and highly conductive material, and examples of such a material are indium tin oxide (ITO), indium zinc oxide(IZO), tin oxide ($SnO_2$), and zinc oxide (ZnO). When the first electrode 110 is a semi-transmissive electrode or a reflective electrode, at least one selected from magnesium (Mg), aluminum (Al), aluminum-lithium (Al—Li), calcium (Ca), magnesium-indium (Mg—In), and magnesium-silver (Mg—Ag).

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

The organic layer 150 may be disposed on the first electrode 110. The organic layer 150 may include an emission layer.

The organic layer 150 may further include a hole transport region between the first electrode 110 and the emission layer, and an electron transport region between the emission layer and the second electrode 190.

The hole transport region may include at least one selected from a hole transport layer, a hole injection layer, a buffer layer, and an electron blocking layer, and the electron transport region may include at least one selected from a hole blocking layer, an electron transport layer, and an electron injection layer. However, it may be understood that embodiments are not limited thereto.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a hole injection layer/hole transport layer structure, a hole injection layer/hole transport layer/buffer layer structure, a hole injection layer/buffer layer structure, a hole transport layer/buffer layer structure, or a hole injection layer/hole transport layer/electron blocking layer structure, wherein layers of each structure are sequentially stacked from the first electrode 110 in this stated order, but are not limited thereto.

When the hole transport region includes a hole injection layer, the hole injection layer may be formed on the first electrode 110 by using one or more suitable methods selected from vacuum deposition, spin coating, casting, a Langmuir-Blodgett (LB) deposition method, ink-jet printing, laser-printing, and/or laser-induced thermal imaging (LITI).

When the hole injection layer is formed by vacuum deposition, for example, the vacuum deposition may be performed at a deposition temperature of about 100 to about 500° C., at a vacuum degree of about $10^{-8}$ to about $10^{-3}$ torr, and at a deposition rate of about 0.01 to about 100 Å/sec by taking into account the compound for the hole injection layer to be deposited, and the structure of the hole injection layer to be formed.

When the hole injection layer is formed by spin coating, the spin coating may be performed at a coating rate of about 2,000 rpm to about 5,000 rpm, and at a temperature of about 80° C. to 200° C. by taking into account the compound for the hole injection layer to be deposited, and the structure of the hole injection layer to be formed.

When the hole transport region includes a hole transport layer, the hole transport layer may be formed on the first electrode 110 or the hole injection layer by using one or more suitable methods selected from vacuum deposition, spin coating, casting, an LB deposition method, ink-jet printing, laser-printing, and/or LITI. When the hole transport layer is formed by vacuum deposition or spin coating, deposition and coating conditions for the hole transport layer may be the same as the deposition and coating conditions for the hole injection layer.

The hole transport region may include at least one selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine) (TC-TA), polyaniline/dodecylbenzenesulfonic acid (Pani/DBSA), poly(3,4-ethylenedioxythiophene)/poly(4-styrene-sulfonate) (PE DOT/PSS), polyaniline/camphor sulfonic acid (Pani/CSA), and polyaniline/poly(4-styrenesulfonate) (Pani/PSS):

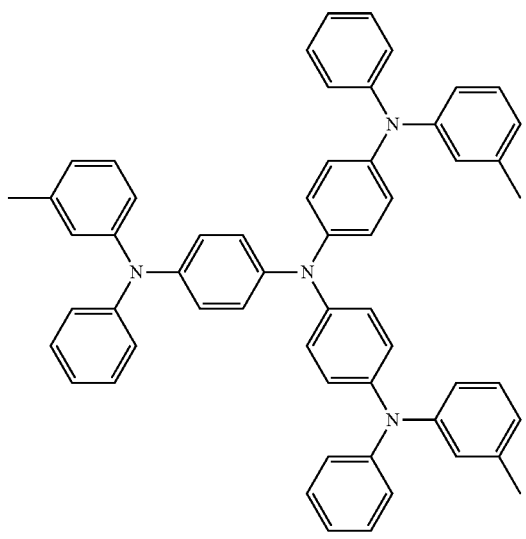

m-MTDATA

-continued
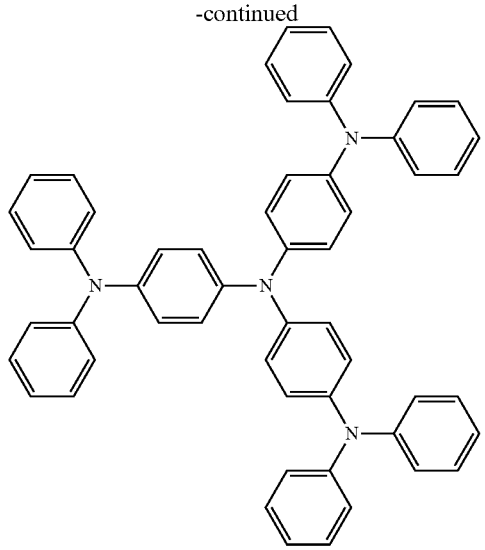
TDATA
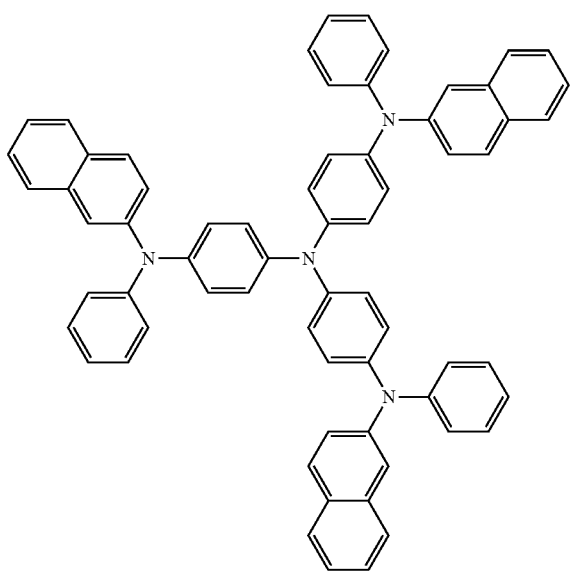
2-TNATA
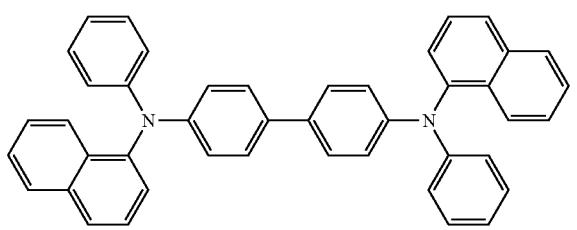
NPB
-continued
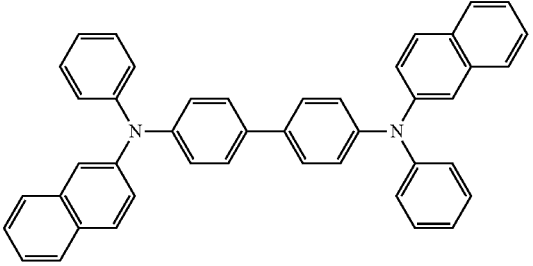
β-NPB
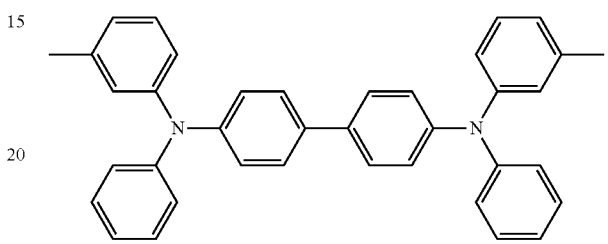
TPD
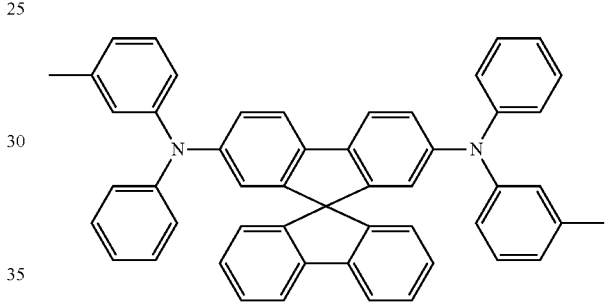
Spiro-TPD
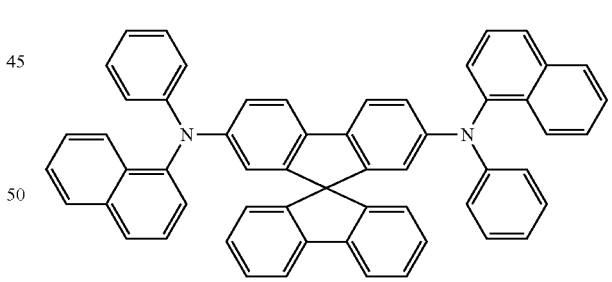
Spiro-NPB
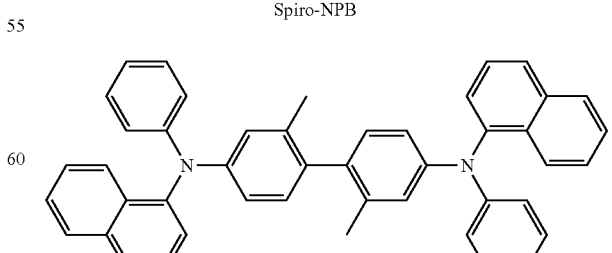
α-NPB

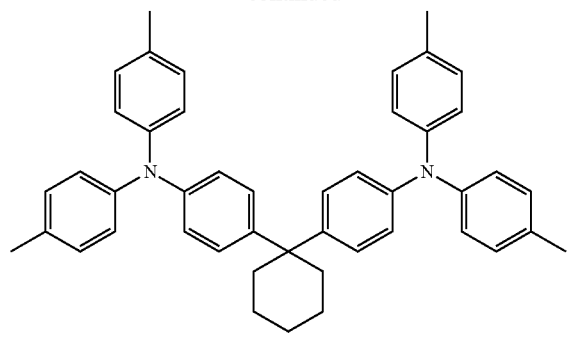

TAPC

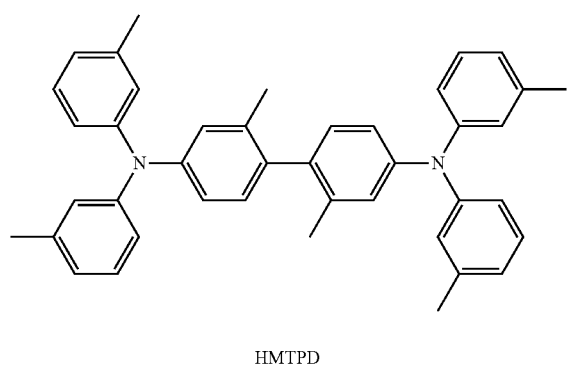

HMTPD

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below, but are not limited thereto:

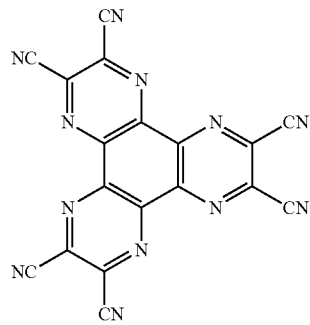

<Compound HT-D1>

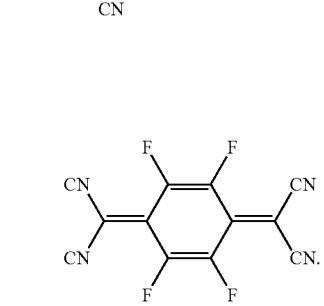

<F4-TCNQ>

The hole transport region may further include a buffer layer, in addition to an electron blocking layer, a hole injection layer, and a hole transport layer. Since the buffer layer may compensate for an optical resonance distance according to a wavelength of light emitted from the emission layer, light-emission efficiency of a formed organic light-emitting device may be improved. For use as a material included in the buffer layer, materials that are to be included in the hole transport region may be used. The electron blocking layer prevents injection of electrons from the electron transport region.

An emission layer may be formed on the first electrode 110 or the hole transport region by using one or more suitable methods selected from vacuum deposition, spin coating, casting, an LB deposition method, ink-jet printing, laser-printing, and/or LITI. When an emission layer is formed by vacuum deposition or spin coating, deposition and coating conditions for the emission layer may be the same as those for the hole injection layer.

When the organic light-emitting device 10 is a full color organic light-emitting device, the emission layer may be patterned into a red emission layer, a green emission layer, or a blue emission layer, according to a sub-pixel. In one or more embodiments, the emission layer may have a stacked structure including a red emission layer, a green emission layer, and a blue emission layer, or may include a red light-emitting material, a green light-emitting material, and a blue light-emitting material, which are mixed with each other in a single layer, to emit white light.

The emission layer may include a host and a dopant.

The host may include the compound of Formula 1 according to an embodiment.

The dopant may be, for example, a known fluorescent dopant.

The fluorescent dopant may include at least one selected from DPAVBi, BDAVBi, TBPe, DCM, DCJTB, Coumarin 6, and C545T:

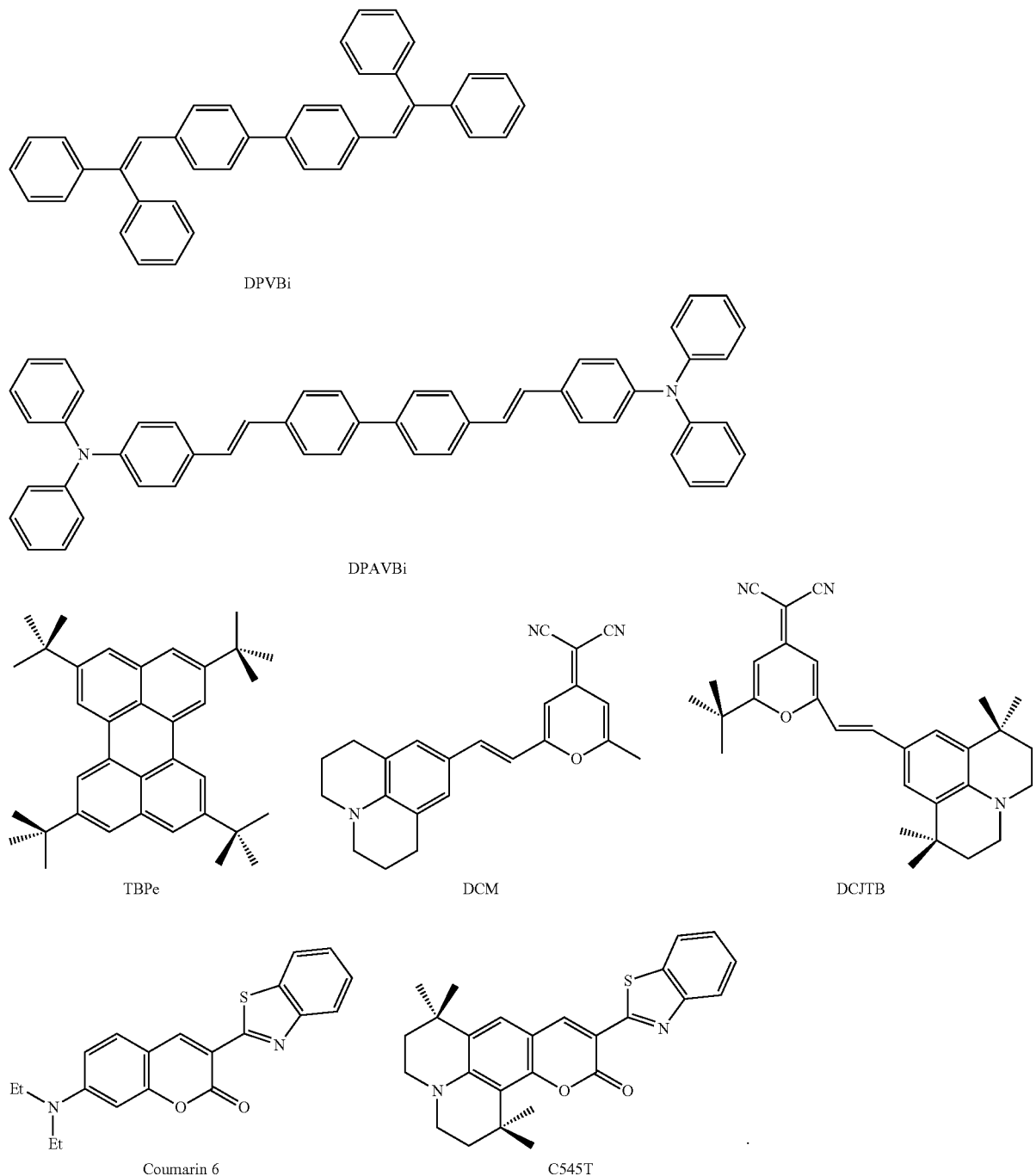

In one or more embodiments, the fluorescent dopant may include a compound represented by Formula 501:

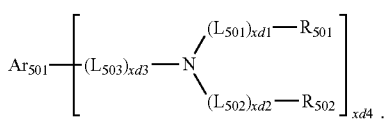

<Formula 501>

In Formula 501,

Ar$_{501}$ may be selected from:

a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, a naphthalene group, a heptalene group, a fluorene group, a spiro-fluorene group, a benzofluorene group, a dibenzofluorene group, a phenalene group, a phenanthrene group, an anthracene, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (wherein $Q_{501}$ to $Q_{503}$ may each independently be selected from hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group), descriptions of $L_{501}$ to $L_{503}$ are the same as the descriptions provided herein in connection with L301, $R_{501}$ and $R_{502}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group and a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may each independently be selected from 0, 1, 2, and 3, and xb4 may be selected from 1, 2, 3, and 4.

An amount of the dopant in the emission layer may be, in general, in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer, but is not limited thereto.

When the electron transport region includes a hole blocking layer, the hole blocking layer may be formed on the emission layer by using one or more suitable methods selected from vacuum deposition, spin coating, casting, an LB deposition method, ink-jet printing, laser-printing, and/or LITI. When the hole blocking layer is formed by vacuum deposition or spin coating, deposition and coating conditions for the hole blocking layer may be determined by referring to the deposition and coating conditions for the hole injection layer.

The hole blocking layer may include, for example, at least one of BCP and Bphen, but is not limited thereto:

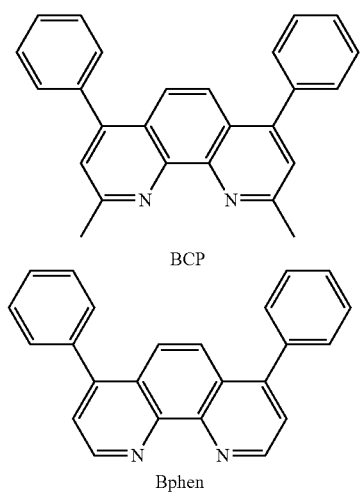

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport region may have an electron transport layer/electron injection layer structure or a hole blocking layer/electron transport layer/electron injection layer structure, wherein layers of each structure are sequentially stacked from the emission layer in the stated order, but the structure thereof is not limited thereto.

In an embodiment, the organic layer 150 of the organic light-emitting device 10 may include an electron transport region between the emission layer and the second electrode 190, and the electron transport region may include an electron transport layer. The electron transport layer may include a plurality of layers. For example, the electron transport region may include a first electron transport layer and a second electron transport layer.

In an embodiment, the electron transport region may include the compound of Formula 1 according to an embodiment.

In another embodiment, the electron transport layer may include the compound of Formula 1 according to an embodiment.

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material (for example, a metal complex).

The metal-containing material may include a Li complex. The Li complex may include, for example, Compound ET-D1 (lithium quinolate, LiQ) or Compound ET-D2:

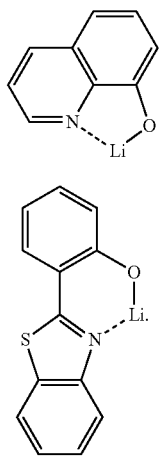

The electron transport region may include an electron injection layer that facilitates injection of electrons from the second electrode 190.

The electron injection layer may be formed on the electron transport layer by using one or more suitable methods selected from vacuum deposition, spin coating, casting, an LB deposition method, ink-jet printing, laser-printing, and/or LITI. When the electron injection layer is formed by vacuum deposition or spin coating, deposition and coating conditions for the electron injection layer may be the same as those for the hole injection layer.

The electron injection layer may include at least one selected from LiF, NaCl, CsF, Li$_2$O, BaO, and LiQ.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 190 may be disposed on the organic layer 150. The second electrode 190 may be a cathode which is an electron injection electrode, and in this regard, a material for forming the second electrode 190 may be selected from metal, an alloy, an electrically conductive compound, and a mixture thereof, which have a relatively low work function. Examples of the material for forming the second electrode 190 are Li, Mg, Al, Al—Li, Ca, Mg—In, and Mg—Ag. In one or more embodiments, the material for forming the second electrode 190 may be ITO or IZO. The second electrode 190 may be a reflective electrode, a semi-transmissive electrode, or a transmissive electrode.

Also, an organic layer according to an embodiment may be formed by depositing the compound according to an embodiment, or may be formed by using a wet method in which the compound according to an embodiment is prepared in the form of solution and then the solution of the compound is used for coating.

An organic light-emitting device according to an embodiment may be used in various flat panel display apparatuses, such as a passive matrix organic light-emitting display apparatus or an active matrix organic light-emitting display apparatus. For example, when the organic light-emitting device is included in an active matrix organic light-emitting display apparatus, a first electrode disposed on a substrate acts as a pixel and may be electrically connected to a source electrode or a drain electrode of a thin film transistor. In addition, the organic light-emitting device may be included in a flat panel display apparatus that emits light in opposite directions.

Hereinbefore, the organic light-emitting device has been described with reference to FIG. 1, but is not limited thereto.

Hereinafter, definitions of substituents of compounds used herein will be presented (the number of carbon atoms used to restrict a substituent is not limited, and does not limit properties of the substituent, and unless defined otherwise, the definition of the substituent is consistent with a general definition thereof).

The term "C$_1$-C$_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a ter-butyl group, a pentyl group, an iso-amyl group, and a hexyl group. The term "C$_1$-C$_{60}$ alkylene group" as used herein refers to a divalent group having the same structure as the C$_1$-C$_{60}$ alkyl group.

The term "C$_1$-C$_{60}$ alkoxy group" as used herein refers to a monovalent group represented by —OA$_{101}$ (wherein A$_{101}$ is the C$_1$-C$_{60}$ alkyl group), and examples thereof include a methoxy group, an ethoxy group, and an isopropyloxy group.

The term "C$_2$-C$_{60}$ alkenyl group" as used herein refers to a hydrocarbon group having at least one carbon-carbon double bond in the middle or at the terminus of the C$_2$-C$_{60}$ alkyl group, and examples thereof include an ethenyl group, a prophenyl group, and a butenyl group. The term "C$_2$-C$_{60}$ alkenylene group" as used herein refers to a divalent group having the same structure as the C$_2$-C$_{60}$ alkenyl group.

The term "C$_2$-C$_{60}$ alkynyl group" as used herein refers to a hydrocarbon group having at least one carbon-carbon triple bond in the middle or at the terminus of the C$_2$-C$_{60}$ alkyl group, and examples thereof include an ethynyl group and a propynyl group. The term "C$_2$-C$_{60}$ alkynylene group" as used herein refers to a divalent group having the same structure as the C$_2$-C$_{60}$ alkynyl group.

The term "C$_3$-C$_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "C$_3$-C$_{10}$ cycloalkylene group" as used herein refers to a divalent group having the same structure as the C$_3$-C$_{10}$ cycloalkyl group.

The term "C$_1$-C$_{10}$ heterocycloalkyl group" as used herein refers to a monovalent saturated monocyclic group having at least one heteroatom selected from N, O, P, and S as a ring-forming atom and 1 to 10 carbon atoms, and examples thereof include a tetrahydrofuranyl group, and a tetrahydrothiophenyl group. The term "$C_2$-$C_{10}$ heterocycloalkylene group" as used herein refers to a divalent group having the same structure as the $C_2$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_2$-$C_{10}$ heterocycloalkenyl group" as used herein refers to a monovalent monocyclic group that has at least one heteroatom selected from N, O, P, and S as a ring-forming atom, 2 to 10 carbon atoms, and at least one carbon-carbon double bond in its ring. Examples of the $C_2$-$C_{10}$ heterocycloalkenyl group include a 2,3-dihydrofuranyl group and a 2,3-dihydrothiophenyl group. The term "$C_2$-$C_{10}$ heterocycloalkenylene group" as used herein refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a carbocyclic aromatic system that has at least one heteroatom selected from N, O, P, and S as a ring-forming atom, in addition to 2 to 60 carbon atoms. The term "$C_1$-$C_{60}$ heteroarylene group" as used herein refers to a divalent group having a carbocyclic aromatic system that has at least one heteroatom selected from N, O, P, and S as a ring-forming atom, in addition to 2 to 60 carbon atoms. Examples of the $C_1$-$C_{60}$ heteroaryl group a ring-forming atom, in addition to 2 to 60 carbon atoms. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. An example of the monovalent non-aromatic condensed polycyclic group includes a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, has a heteroatom selected from N, O, P, and S, other than carbon atoms, as a ring-forming atom, and has no aromaticity in its entire molecular structure. An example of the monovalent non-aromatic condensed heteropolycyclic group includes a carbazolyl group. The term "divalent non-aromatic condensed heteropolycyclic group" as used herein refers to a divalent group having the same structure as the monovalent non-aromatic condensed heteropolycyclic group.

In the present specification, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group(aryloxy), $C_6$-$C_{60}$ arylthio group(arylthio), $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, and $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —$N(Q_{11})(Q_{12})$, —$Si(Q_{13})(Q_{14})(Q_{15})$, and —$B(Q_{16})(Q_{17})$, a cyclopenlyl group, a cyclohexyl group, a cycloheptyl group, a cyclopentenyl group, a cyclohexenyl group, a phenyl group, a pentalenyl group, an indenyl group, a naphlhyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group a fluoranthenyl group, a tnphenylenyl group, a pyrenyl group a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F. —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group a fluoranthenyl group, a triphenylenyl group, a pyrenyl group a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), and $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The expression "Ph" used herein refers to a phenyl group, the expression "Me" used herein refers to a methyl group, the expression "Et" used herein refers to an ethyl group, and the expression "ter-Bu" or "But" used herein refers to a tert-butyl group.

Hereinafter, an organic light-emitting device according to an embodiment will be described in detail with reference to Synthesis Examples and Examples.

SYNTHESIS EXAMPLES

Synthesis Example 1

Synthesis of Intermediate A

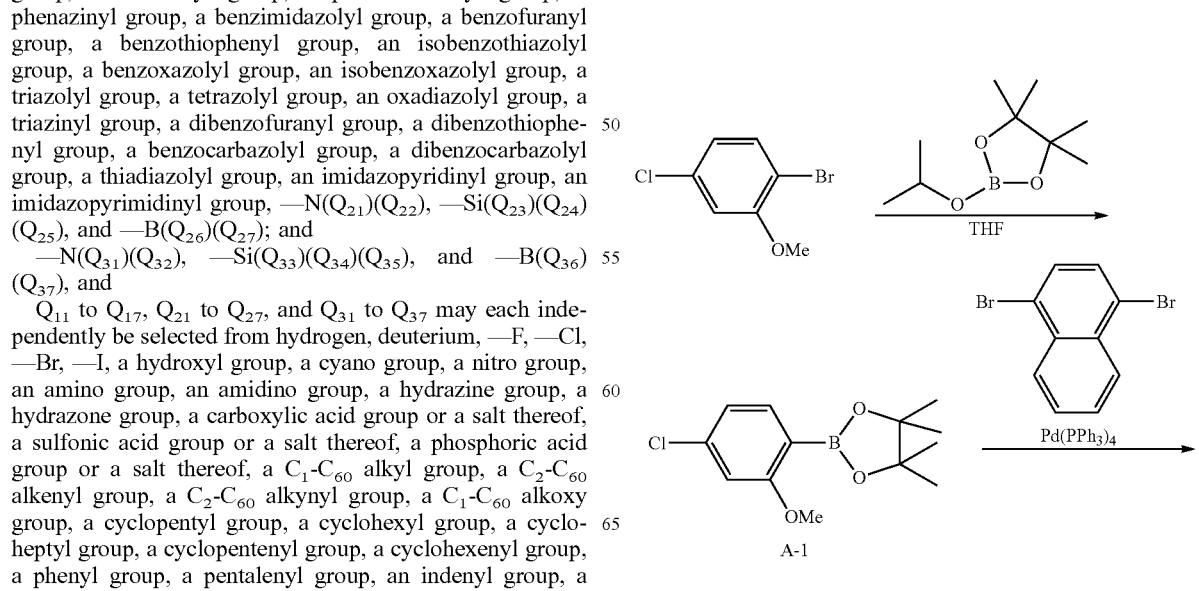

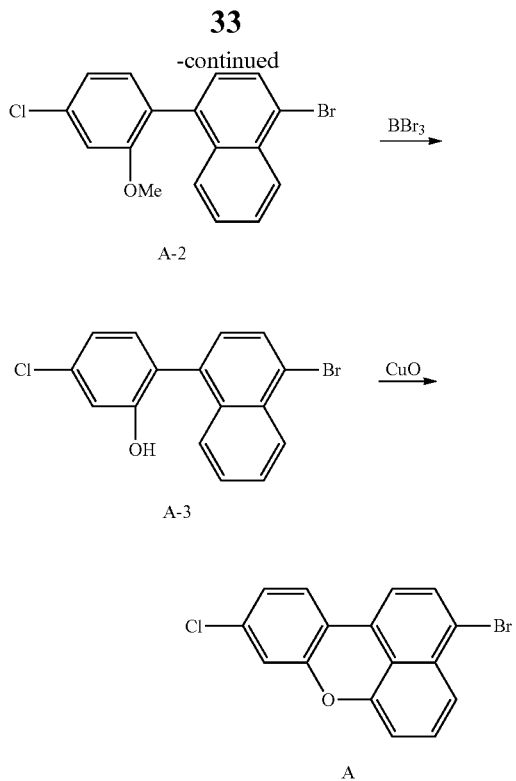

A-2

A-3

A

Synthesis of Intermediate A-1

6.4 g (30 mmol) of 2-bromo-5-chloroanisol was dissolved in 150 ml of THF, and then, at a temperature of −78° C., 12 ml of n-BuLi (30.0 mmol, 2.5 M in Hexane) was slowly dropped thereto. At the same temperature, the resultant solution was stirred for 1 hour, and then, 6.7 ml (36.0 mmol) of 2-isoproxy-4,4,5,5,-tetramethyl-1,3,2-dioxaborolane was slowly added thereto. The reaction solution was stirred at a temperature of −78° C. for 1 hour, and then, additionally stirred at room temperature for 24 hours. After the reaction was stopped, 50 ml of 10% HCl aqueous solution and 50 ml of H₂O were added thereto, and an extraction process was performed thereon three times by using 80 ml of diethylether. An organic layer collected therefrom was dried by using magnesium sulfate and the residual obtained by evaporating a solvent therefrom was separation-purified by silica gel chromatography to obtain 7.25 g (yield: 90%) of Intermediate A-1.

Synthesis of Intermediate A-2

7.25 g (27.0 mmol) of Intermediate A-1, 11.6 g (40.5 mmol) of 1,4-dibromonaphthalene, 1.27 g (1.1 mmol) of Pd(PPh₃)₄, and 6.82 g (50 mmol) of K₂CO₃ were dissolved in 200 ml of a mixed solution of THF/H₂O (at a volume ratio of 2/1), and then, the resultant solution was stirred at a temperature of 70° C. for 5 hours. After the reaction solution was cooled to room temperature, 60 ml of water was added thereto, and an extraction process was performed thereon three times by using 60 ml of ethylether. An organic layer collected therefrom was dried by using magnesium sulfate, and then, the residual obtained by evaporating a solvent therefrom was separation-purified by silica gel chromatography to obtain 7.65 g (yield: 81.5%) of Intermediate A-2.

Synthesis of Intermediate A-3

6.96 g (20 mmol) of Intermediate A-2 was dissolved in 200 ml of dichloromethane, and then, the resultant solution was stirred at a temperature of 0° C. for 1 hour. 30 ml (30.0 mmol, 1M in Tol) of BBr₃ was dropped thereto for 30 minutes, and the reaction solution was stirred at room temperature for 2 hours. 50 ml of water was added thereto, and then, an extraction process was performed thereon three times by using 50 ml of dichloromethane. An organic layer collected therefrom was dried by using magnesium sulfate, and then, the residual obtained by evaporating a solvent therefrom was separation-purified by silica gel chromatography to obtain 6.55 g (yield: 95%) of Intermediate A-3.

Synthesis of Intermediate A 6.55 g (19.5 mmol) of Intermediate A-3 was dissolved in 50 ml of nitrobenzene, and then, at room temperature, 7.8 g (100 mmol) of CuO was added thereto. The reaction solution was stirred at a temperature of 190° C. for 48 hours. After the reaction was stopped, the reaction solution was filtered by using cellite, and then, 10 ml of water was added to an organic layer collected therefrom, and an extraction process was performed thereon three times by using 30 ml of ethylacetate. An organic layer collected therefrom was dried by using magnesium sulfate and the residual obtained by evaporating a solvent therefrom was separation-purified by silica gel chromatography to obtain 4.634 g (yield: 71%) of Intermediate A.

Synthesis Example 2

Synthesis of Compound 1

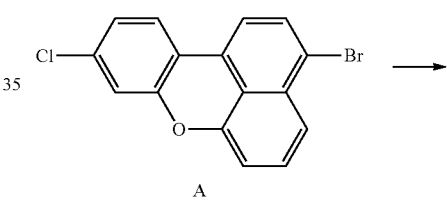

A

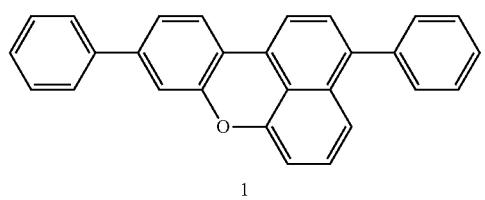

1

Synthesis of Compound 1

1.65 g (5 mmol) of Intermediate A, 1.81 g (15 mmol) of phenylboronic acid, 2.26 g (15 mmol) of CsF, and 1.84 g (0.25 mmol) of PdCl₂(PCy₃)₂ were dissolved in 100 ml of NMP, and the resultant solution was stirred at a temperature of 150° C. for 24 hours. After the reaction solution was cooled to room temperature, 60 ml of water was added thereto, and an extraction process was performed thereon three times by using 60 ml of ethylether. An organic layer collected therefrom was dried by using magnesium sulfate, and then, the residual obtained by evaporating a solvent therefrom was separation-purified by silica gel chromatography to obtain 1.11 g (yield: 60%) of Compound 1.

¹H NMR (CDCl₃, 400 MHz) δ (ppm): 8.20(d, 1H), 8.00-7.85(m, 5H), 7.65-7.50 (m, 6H), 7.40-7.30 (m, 4H), 7.22-7.20(m, 1H), 6.88 (dd, 1H)

Synthesis Example 3

Synthesis of Compound 5

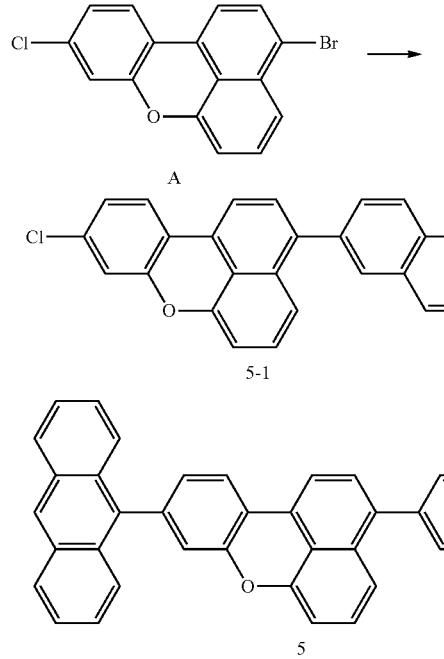

Synthesis of Intermediate 5-1

1.89 g (yield: 71%) of Intermediate 5-1 was synthesized in the same manner as in Synthesis of Intermediate A-2, except that 2-naphthalene boronic acid and Intermediate A were used instead of Intermediate A-1 and 1,4-dibromonaphthalene, respectively.

Synthesis of Compound 5

1.56 g (yield: 67%) of Compound 5 was synthesized in the same manner as in Synthesis of Compound 1, except that Intermediate 5-1 and 9-anthracene boronic acid were used instead of Intermediate A and phenylboronic acid, respectively.

$^1$H NMR (CDCl$_3$, 400 MHz) δ (ppm): 8.40 (s, 1H), 8.20(d, 1H), 8.15(dd, 3H), 8.05-7.85(m, 9H), 7.70-7.60 (m, 4H), 7.50-7.45 (m, 2H), 7.22(d, 1H), 7.15-7.05 (m, 3H)

Synthesis Example 4

Synthesis of Compound 21

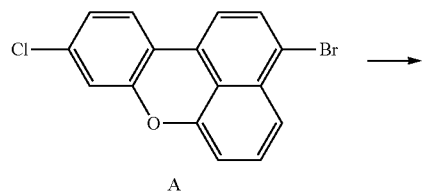

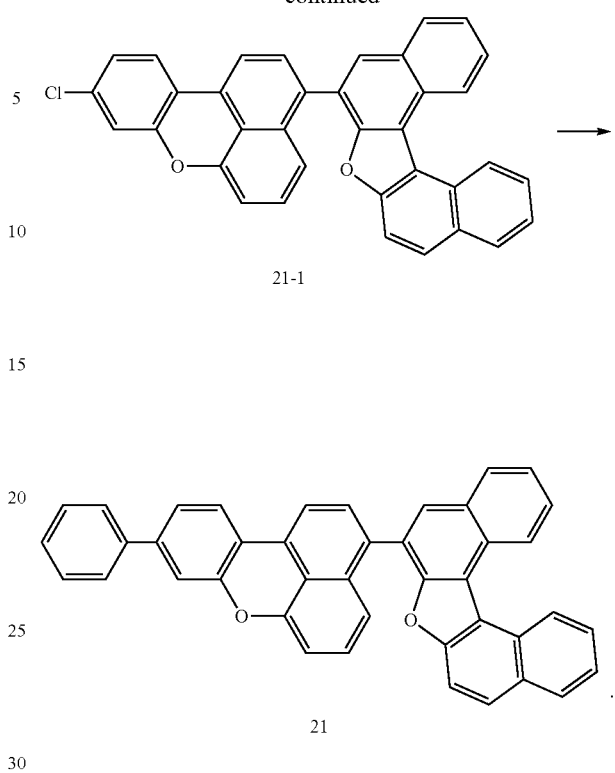

Synthesis of Intermediate 21-1

1.76 g (yield: 85%) of Intermediate 21-1 was synthesized in the same manner as in Synthesis of Intermediate A-2, except that dinaphtho[2,1-b:1',2'-d]furan-6-yl boronic acid and Intermediate A were used instead of Intermediate A-1 and 1,4-dibromonaphthalene, respectively.

Synthesis of Compound 21

1.4 g (yield: 73%) of Compound 21 was synthesized in the same manner as in Synthesis of Compound 1, except that Intermediate 21 was used instead of Intermediate A.

$^1$H NMR (CDCl$_3$, 400 MHz) δ (ppm): 8.50(dd, 2H), 8.40 (d, 1H), 8.20(d, 2H), 8.10-7.85(m, 8H), 7.75-7.65 (m, 4H), 7.60-7.45 (m, 5H), 7.30-7.25(m, 1H), 7.15 (t, 1H)

Synthesis Example 5

Synthesis of Compound 39

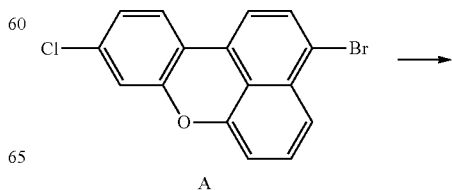

-continued

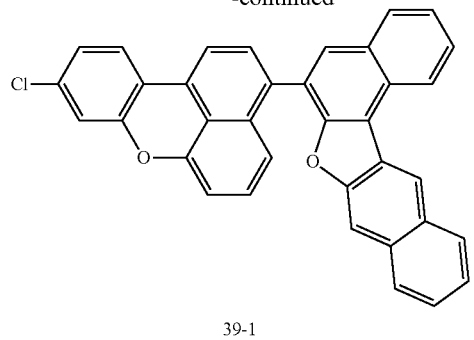

39-1

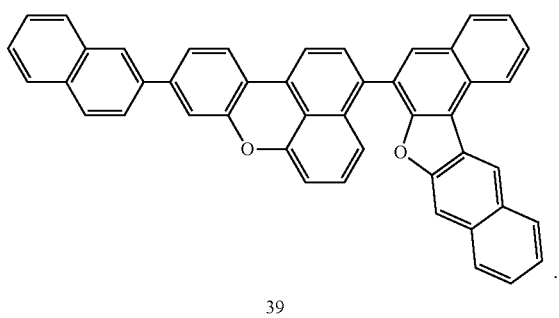

39

Synthesis of Intermediate 39-1

1.65 g (yield: 80%) of Intermediate 39-1 was used synthesized in the same manner as in Synthesis of Intermediate A-2, except that dinaphtho[2,1-b:2',3'-d]furan-6-yl boronic acid and intermediate A were used instead of Intermediate A-1 and 1,4-dibromonaphthalene, respectively.

Synthesis of Compound 39

1.74 g (yield: 77%) of Compound 39 was used synthesized in the same manner as in Synthesis of Compound 1, except that Intermediate 39-1 and 2-naphthaleneboronic acid were used instead of Intermediate A and phenylboronic acid, respectively.

$^1$H NMR (CDCl$_3$, 400 MHz) δ (ppm): 8.50(d, 1H), 8.40 (s, 1H), 8.35(d, 1H), 8.30(t, 2H), 8.20-8.10(m, 3H), 8.05-7.85(m, 7H), 7.65-7.35 (m, 10H), 7.15 (t, 1H)

Other additional compounds were synthesized by using synthetic methods equivalent to those described above and using appropriate intermediate materials.

EXAMPLES

Example 1

An anode was manufactured by cutting a Corning 15 Ω/cm$^2$ (1,200 Å) ITO glass substrate to a size of 50 mm×50 mm×0.7 mm, ultrasonically cleaning the glass substrate by using isopropyl alcohol and pure water for 5 minutes each, and then, irradiating UV light for 30 minutes thereto and being exposed to ozone to clean. Then, the anode was loaded into a vacuum deposition apparatus.

Then, 2-TNATA, which is a known material, was vacuum deposited thereon to form a hole injection layer having a thickness of 600 Å, and then, 4,4'bis[N-(1-naphthyl)-N-phenylamino]biphenyl (hereinafter, also referred to as NPB), which is a known hole transport compound, was vacuum deposited thereon to form a hole transport layer having a thickness of 300 Å.

On the hole transport layer, Compound 1, which is blue fluorescent host, and 4,4'-bis[2-(4-(N,N-diphenylamino) phenyl)vinyl]biphenyl] (hereinafter, referred to as DPAVBi), which is a known blue fluorescent dopant, were co-deposited at a weight ratio of 98:2 to form an emission layer having a thickness of 300 Å.

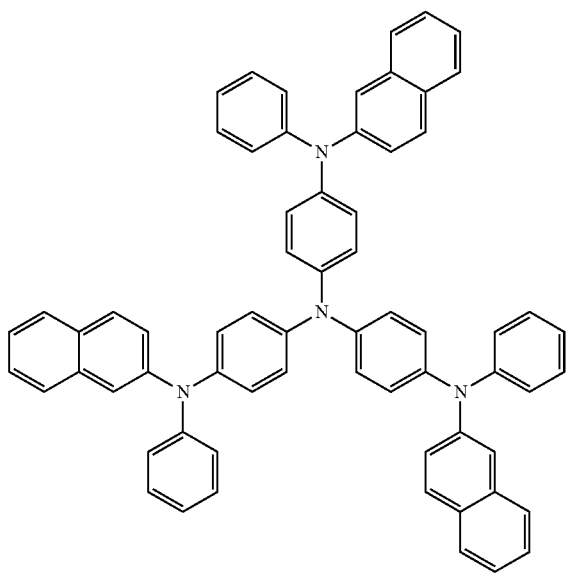

2-TNATA

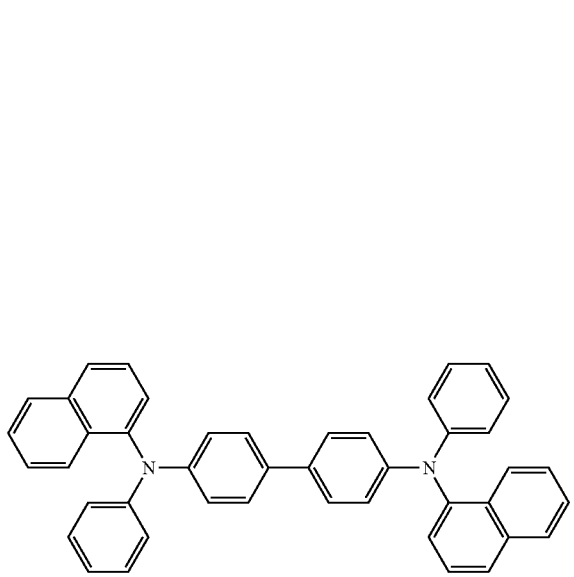

NPB

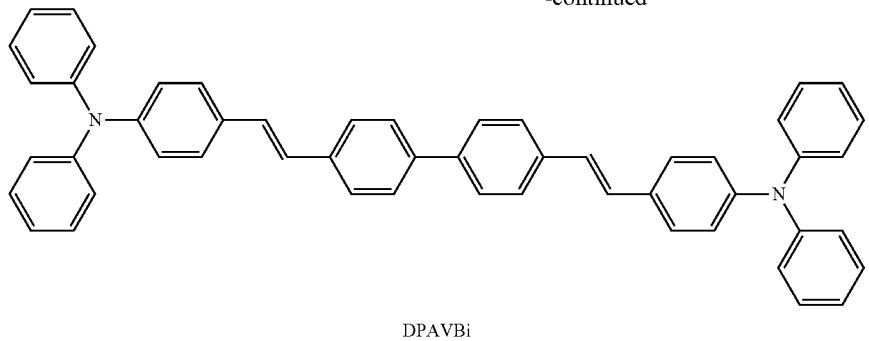

DPAVBi

Then, Alq$_3$ was deposited on the emission layer to form an electron transport layer having a thickness of 300 Å, and then, LiF, which is a halogenated alkali metal, was deposited on the electron transport layer to form an electron injection layer having a thickness of 10 Å, and Al was deposited thereon to a thickness of 3,000 Å (cathode), thereby forming an LiF/Al electrode, thereby completing the manufacturing of an organic light-emitting device.

Comparative Example 1

An organic light-emitting device was manufactured in the same manner as in Example 1, except that in forming the emission layer, DNA, which is a known blue fluorescent host, was used instead of Compound 1.

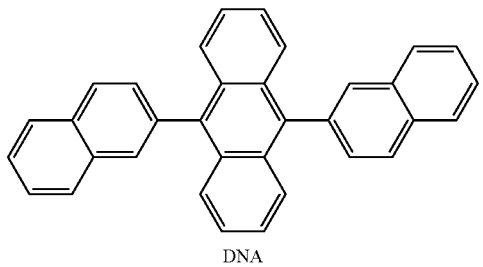

DNA

Example 2

An organic light-emitting device was manufactured in the same manner as in Comparative Example 1, except that in forming the electron transport layer, Compound 5 was used instead of Alq$_3$.

Example 3

An organic light-emitting device was manufactured in the same manner as in Comparative Example 1, except that, as a blue fluorescent host, Compound 21 was used instead of Compound 1.

Example 4

An organic light-emitting device was manufactured in the same manner as in Comparative Example 1, except that, as a blue fluorescent host, Compound 39 was used instead of Compound 1.

Comparative Example 2

An organic light-emitting device was manufactured in the same manner as in Example 2, except that in forming the electron transport layer, Compound 100 was used instead of Compound 5.

Compound 100

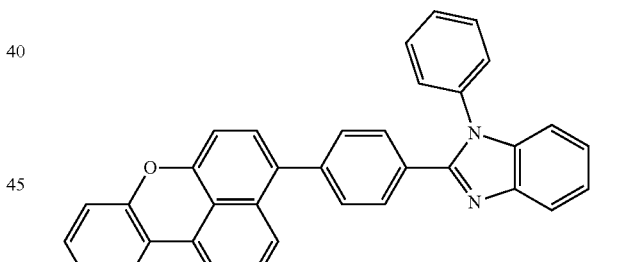

Compounds having structures of Compounds 1, 5, 21, and 39 according to Examples above were each used as a host material or an electron transport material in forming a blue emission layer of an organic light-emitting device. As a result, compared with DNA, which is a known material in the art, and Compound 100, the compounds had an improved driving voltage and excellent I-V-L characteristics with high efficiency, and more particularly, exhibited lifespan improvement effects, and thus, a lifespan of the manufactured organic light-emitting devices was significantly prolonged. Representative characteristics and lifespan results are summarized in Table 1.

TABLE 1

| | Material | Driving voltage (V) | Current density (mA/cm²) | Brightness (cd/m²) | Efficiency (cd/A) | Light-emission color | Half lifespan (hr @100 mA/cm²) |
|---|---|---|---|---|---|---|---|
| Example 1 | Compound 1 | 5.96 | 50 | 3005 | 6.01 | Blue | 315 |
| Example 2 | Compound 5 | 6.02 | 50 | 2995 | 5.99 | Blue | 320 |
| Example 3 | Compound 21 | 5.99 | 50 | 3108 | 6.21 | Blue | 305 |
| Example 4 | Compound 39 | 6.24 | 50 | 3069 | 6.1484 | Blue | 335 |
| Comparative Example 1 | DNA | 7.01 | 50 | 2645 | 5.29 | Blue | 258 |
| Comparative Example 2 | Compound 100 | 6.55 | 50 | 2750 | 5.50 | Blue | 270 |

As described above, a compound represented by Formula 1 according to an embodiment has excellent light-emission characteristics and charge transport capability, and thus, is suitable as a light-emission material or an electron transport material for an organic light-emitting device. In this regard, when the compound of Formula 1 is used in an organic light-emitting device, the organic light-emitting device may have high efficiency, low voltage, high brightness, and long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A compound represented by one of Formula 1 and Compound 28:

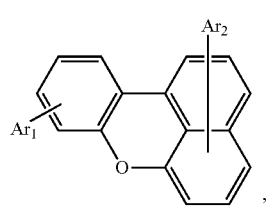

<Formula 1>

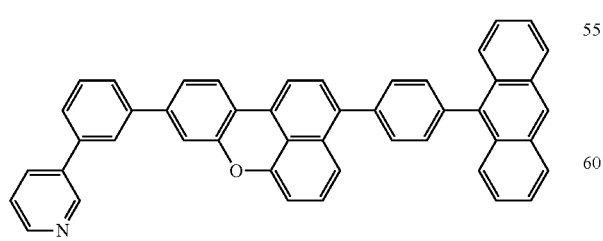

<Compound 28>

28 wherein, in Formula 1,
each of Ar₁ and Ar₂ is independently represented by one of Formulae 2a to 2m:

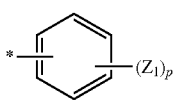

2a

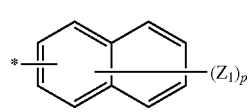

2b

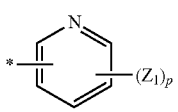

2c

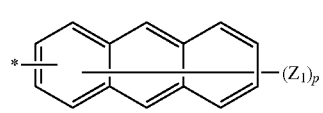

2d

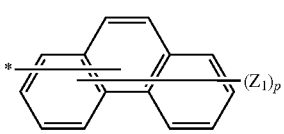

2e

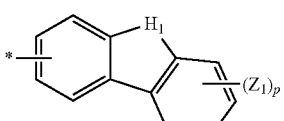

2f

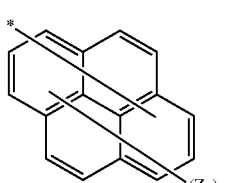

2g

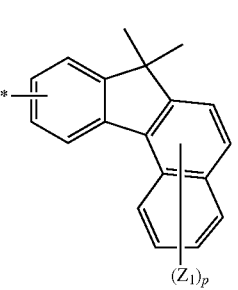

2h

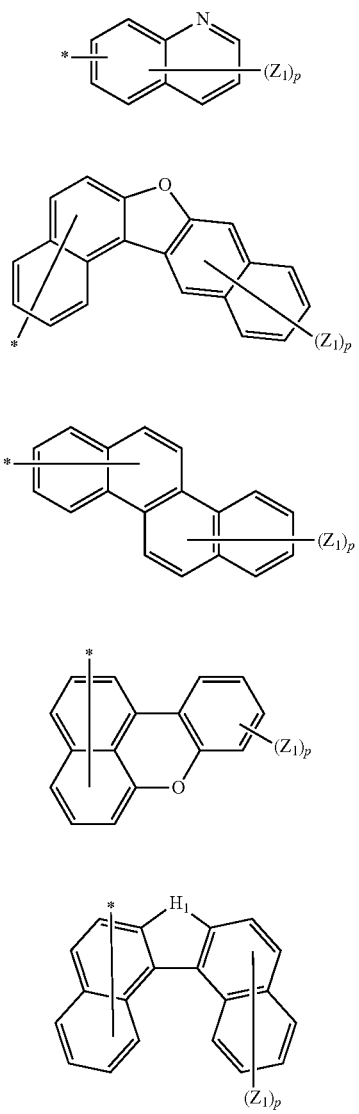

wherein, in Formula 2a to 2m, $H_1$ is $SiR_{21}R_{22}$, $CR_{23}R_{24}$, O, or S, $Z_1$ is selected from hydrogen, deuterium, a cyano group, a substituted or unsubstituted C1-C20 alkyl group, a substituted or unsubstituted C6-C20 aryl group, a substituted or unsubstituted monovalent non-aromatic condensed polycyclic group, and a substituted or unsubstituted monovalent non-aromatic condensed heteropolycyclic group, $SiR_{31}R_{32}R_{33}$, $P(=O)R_{34}R_{35}$, $R_{21}$ to $R_{24}$ and $R_{31}$ to $R_{35}$ are each independently selected from hydrogen, deuterium, a substituted or unsubstituted C1-C20 alkyl group, a substituted or unsubstituted C6-C20 aryl group, a substituted or unsubstituted C1-C20 heteroaryl group, a substituted or unsubstituted monovalent non-aromatic condensed polycyclic group, and a substituted or unsubstituted monovalent non-aromatic condensed heteropolycyclic group, p is an integer of 1 to 9, and

* indicates a binding site.

2. The compound of claim 1, wherein Formula 1 is Formula 2:

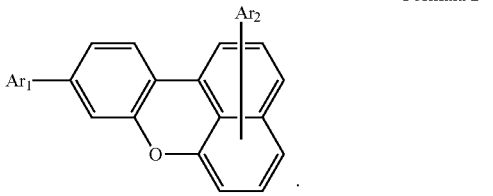

<Formula 2>

3. The compound of claim 1, wherein Formula 1 is Formula 3:

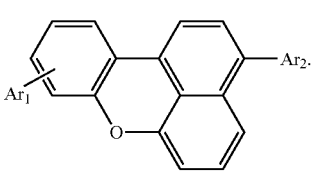

<Formula 3>

4. The compound of claim 1, wherein Formula 1 is Formula 4:

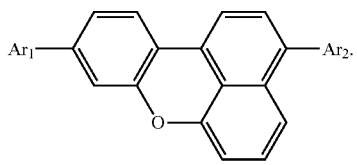

<Formula 4>

5. The compound of claim 1, wherein the compound of Formula 1 is one of compounds illustrated below:

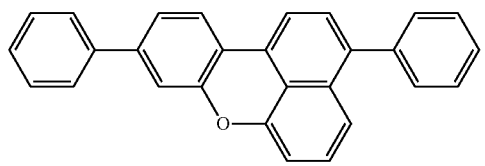

1

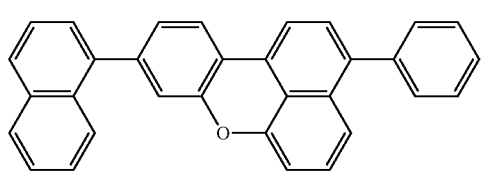

2

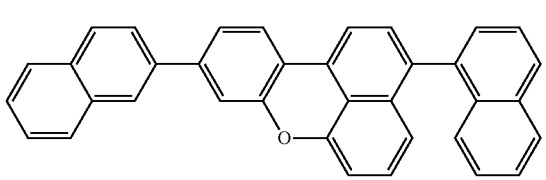

3

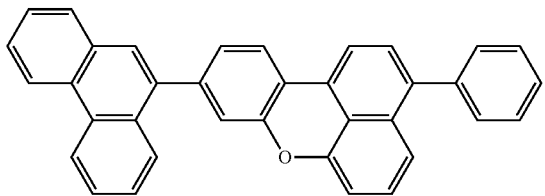
4
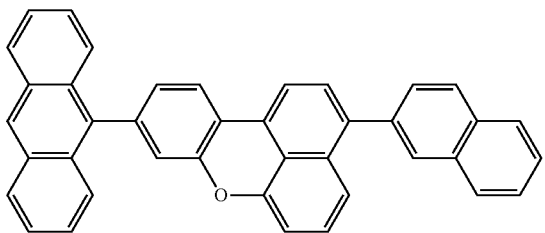
5
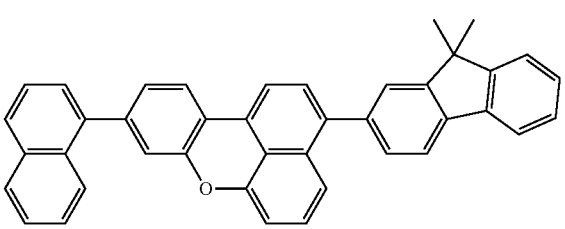
6
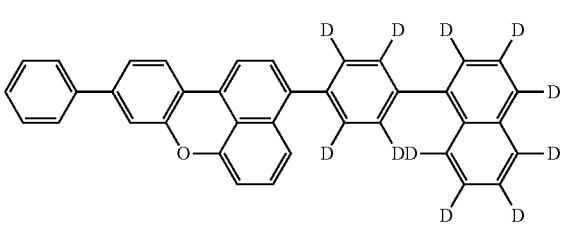
7
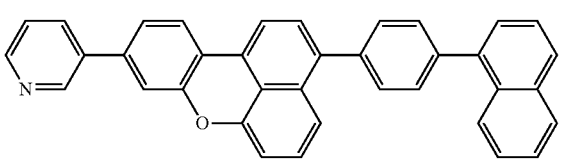
8
9
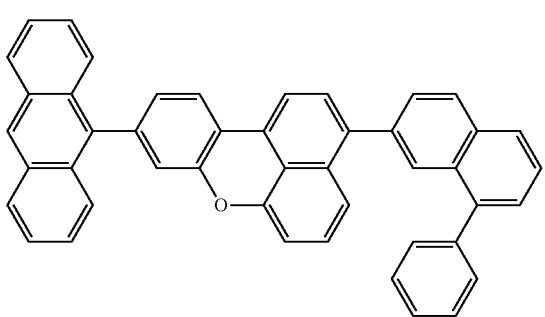
10
11
12
13
14
15
16

17
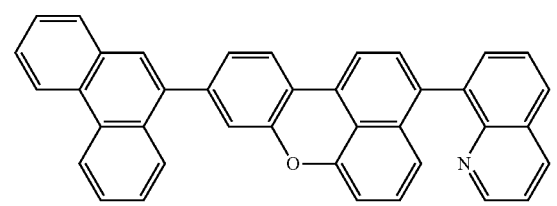
18
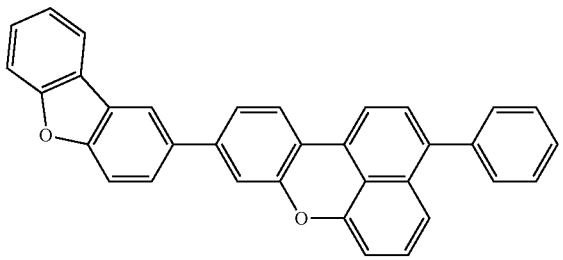
19
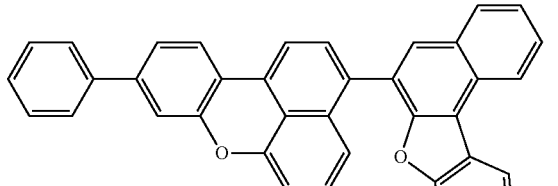
20
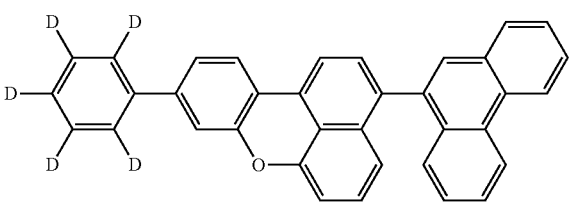
21
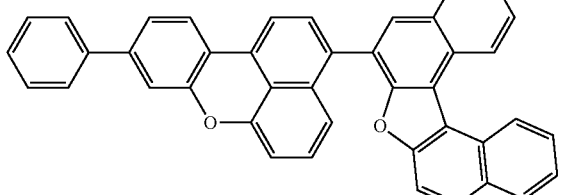
22
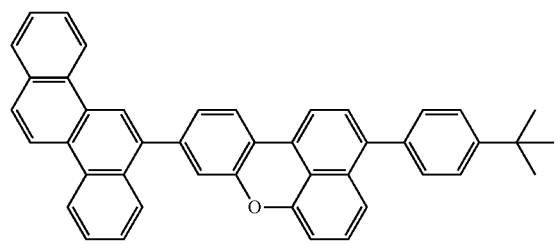
23
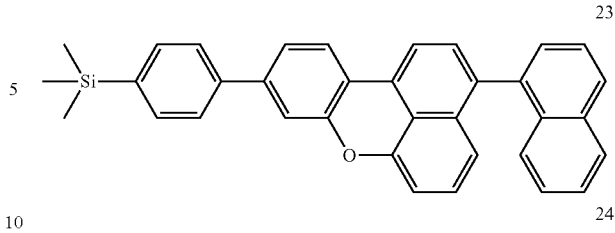
24
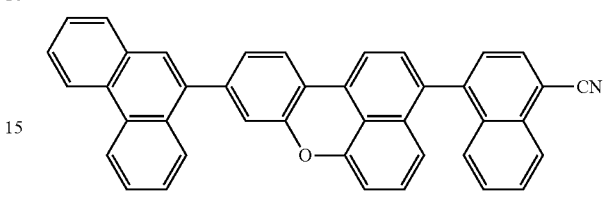
25
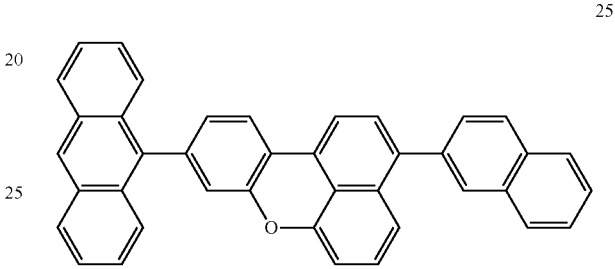
26
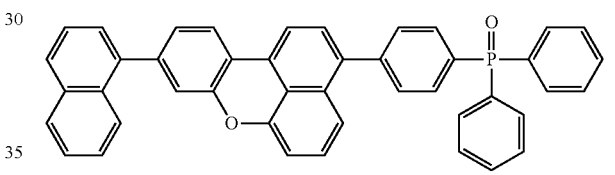
27
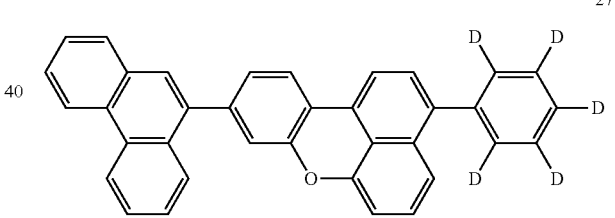
28
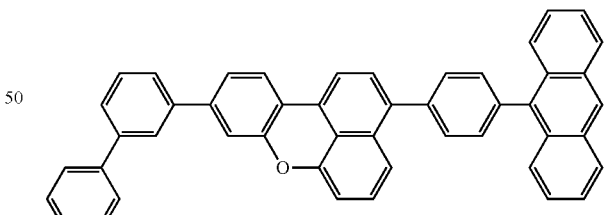
29
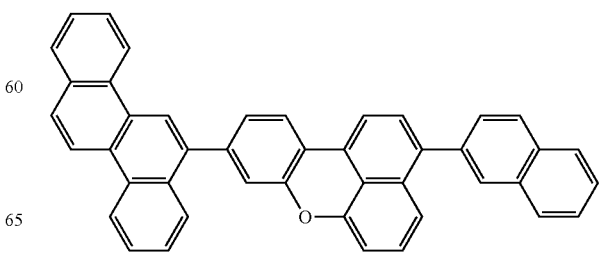

30
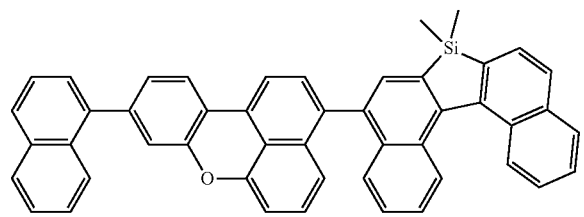

31
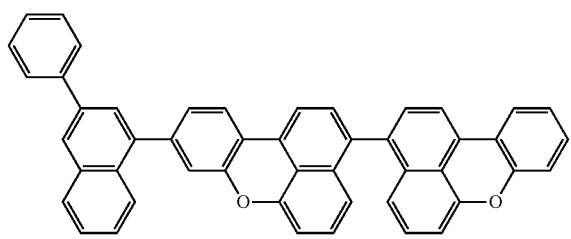

32
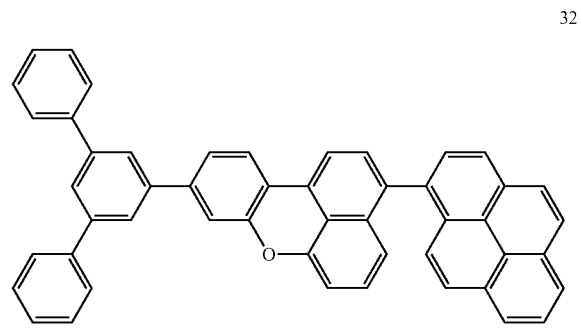

33
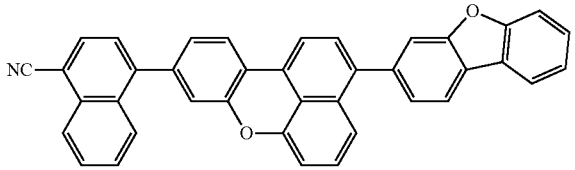

34
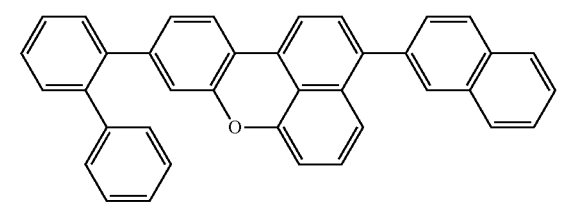

35
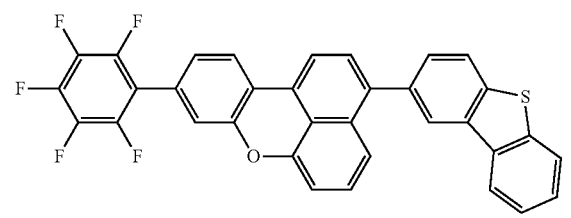

36
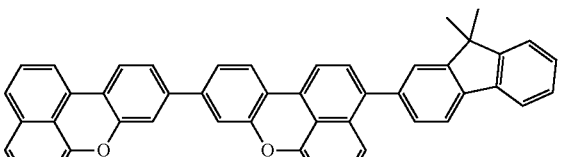

37
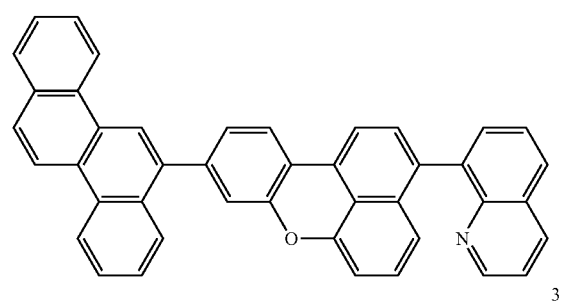

38
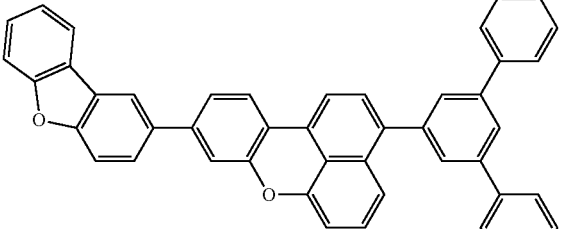

39
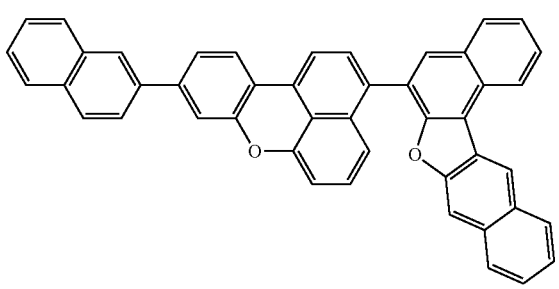

40
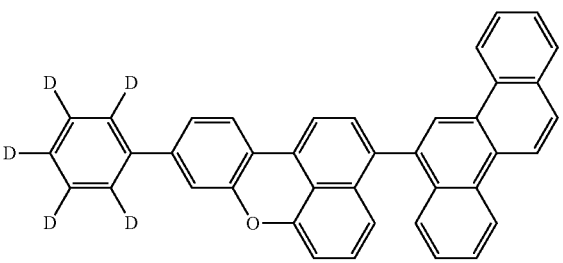

6. An organic light-emitting device comprising:
a first electrode,
a second electrode facing the first electrode, and
an organic layer disposed between the first electrode and the second electrode and comprising an emission layer, wherein the organic layer comprises the compound of claim 1.

7. The organic light-emitting device of claim 6, wherein the first electrode is an anode, the second electrode is a cathode, and the organic layer comprises i) a hole transport region that is disposed between the first electrode and the emission layer and comprises at least one selected from a hole injection layer, a hole transport layer, and an electron blocking layer, and ii) an electron transport region that is disposed between the emission layer and the second electrode and comprises at least one selected from an electron transport layer, a hole blocking layer, and an electron injection layer.

8. The organic light-emitting device of claim 7, wherein the hole transport region comprises a charge-generation material.

9. The organic light-emitting device of claim 8, wherein the charge-generation material is a p-dopant.

10. The organic light-emitting device of claim 9, wherein the p-dopant is at least one selected from a quinone derivative, a metal oxide, and a cyano group-containing compound.

11. The organic light-emitting device of claim 7, wherein the electron transport region comprises a metal complex.

12. The organic light-emitting device of claim 7, wherein the electron transport region comprises a lithium complex.

13. A flat panel display apparatus comprising:
the organic light-emitting device of claim 6,
wherein the first electrode of the organic light-emitting device is electrically connected to a source electrode or a drain electrode of a thin film transistor.

14. An organic light-emitting device comprising:
a first electrode,
a second electrode facing the first electrode, and
an organic layer disposed between the first electrode and the second electrode and comprising an emission layer,
wherein the emission layer comprises the compound of claim 1.

15. The organic light-emitting device of claim 14, wherein the emission layer is a blue emission layer, wherein the blue emission layer comprises the compound of claim 1.

16. The organic light-emitting device of claim 14, wherein the emission layer is a blue emission layer, wherein the blue emission layer comprises the compound of claim 1 as a host.

17. The organic light-emitting device of claim 7, wherein the electron transport region comprises the compound of claim 1.

18. The organic light-emitting device of claim 7, wherein the electron transport layer comprises the compound of claim 1.

* * * * *